United States Patent [19]

Lo et al.

[11] Patent Number: 4,954,269

[45] Date of Patent: Sep. 4, 1990

[54] DIOXOLANE FUNCTIONAL SILICON COMPOUNDS AND METHOD FOR THEIR PREPARATION AND USE

[75] Inventors: Peter Y. K. Lo, Midland; Anthony Revis, Freeland, both of Mich.

[73] Assignee: Dow Corning Corporation, Midland, Mich.

[21] Appl. No.: 377,346

[22] Filed: Jul. 10, 1989

[51] Int. Cl.$^5$ ............................................. D06M 7/00
[52] U.S. Cl. ....................................... 252/86; 252/86; 8/DIG. 1
[58] Field of Search ................... 252/8.6, 8.8, 174.15; 8/137, 581, DIG. 1; 427/387, 393.3, 242

[56] References Cited

U.S. PATENT DOCUMENTS 4,213,908  7/1980  Kotzsch et al. ................ 260/348.16

Primary Examiner—Paul Lieberman
Assistant Examiner—John F. McNally
Attorney, Agent, or Firm—Jim L. DeCesare

[57] ABSTRACT

A method of treating textiles in order to increase the water absorptivity of the textiles involving contacting the textiles with an effective amount of a dioxolane functional organosilicon compound. Representative of the dioxolane or ketal functional organosilicon compounds employed are sym(2,2-dimethyl-4-methyloylpropyl-1,3-dioxolane) disiloxane and sym(2,2-dimethyl-4-methyl-oylpropyl-1,3-dioxolane) polydimethylsiloxane.

17 Claims, No Drawings

DIOXOLANE FUNCTIONAL SILICON COMPOUNDS AND METHOD FOR THEIR PREPARATION AND USE

BACKGROUND OF THE INVENTION

The present invention relates to organosilicon compounds containing dioxolane radicals and to methods for their preparation and use. More specifically, the present invention relates to organosilicon compounds, containing one or more silicon-bonded dioxolane radicals, which are prepared from silicon hydride compounds, and to the use of those organosilicon compounds to provide a substrate with a hydrophilic character.

Ketal or dioxolane functional organosilicon compounds are not new. For example, the prior art discloses such compounds in U.S. Pat. No. 4,213,908, issued July 22, 1980. Specifically, the '908 patent describes a ketal functional silane prepared by the addition of 4-alloxymethyl-1,3-dioxolane onto trialkoxy hydrogen silane or monoalkyl dialkoxy hydrogen silane, using platinum compounds as the catalyst. The addition is said to take place at temperatures of about seventy degrees Centigrade. No utility for such ketal or dioxolane functional organosilicon compounds is disclosed except that the compounds are employed in the preparation of glycidyl products which are said to be useful as adhesives.

In contrast to the '908 patent, the dioxolane compounds of the present invention have been found to have utility in imparting a durable hydrophilic characteristic to textiles such as cotton and polyester fabrics.

SUMMARY OF THE INVENTION

This invention relates to a method of treating textiles in order to increase the water absorptivity of the textiles by contacting the textiles with an effective amount of a dioxolane functional organosilicon compound. For purposes of the present invention, the terms dioxolane functional and ketal functional are employed synonymously.

The invention also relates to a method of treating textiles in order to increase the water absorptivity of the textiles by contacting the textiles with an effective amount of a dioxolane-substituted organosilicon compound containing at least one silicon-bonded dioxolane radical having the formula

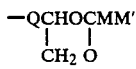

where Q is a divalent organic radical which is bonded to the silicon atom by way of a silicon-carbon bond, M is a monovalent hydrocarbon radical free of aliphatic unsaturation containing from 1 to 6 carbon atoms and M' is H or M; all remaining silicon valences of the dioxolane-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms and divalent radicals joining silicon atoms.

In a specific embodiment of the present invention, the method involves contacting the textiles with an effective amount of a ketal functional organosilicon compound of the formula selected from the group consisting of

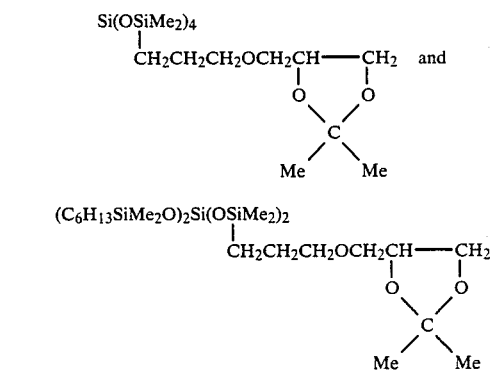

where Me is methyl.

In another specific embodiment of the present invention, the method involves contacting the textiles with an effective amount of a ketal functional organosilicon compound selected from the group consisting of sym[2,2-dimethyl-4-methyloylpropyl-1,3-dioxolane]tetramethyl disiloxane and
sym[2,2-dimethyl-4-methyloylpropyl-1,3-dioxolane]-polydimethylsiloxane.

These and other features, objects, and advantages, of the present invention, will become more apparent from a consideration of the following detailed description thereof.

DETAILED DESCRIPTION OF THE INVENTION

The compounds of this invention are prepared by mixing components comprising (i) an amount of a dioxolane compound having the formula

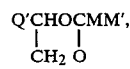

(ii) an amount of a silicon hydride compound containing at least one silicon-bonded hydrogen atom and (iii) an amount of a hydrosilylation catalyst; the conditions of said mixing and the amounts of (i), (ii) and (iii) being sufficient to cause a hydrosilylation reaction to occur between the dioxolane compound and the silicon hydride compound, thereby forming a dioxolane-substituted organosilicon compound containing at least one silicon-bonded dioxolane radical having the formula

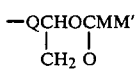

where Q' is a monovalent, aliphatically unsaturated organic radical, M is a monovalent hydrocarbon radical free of aliphatic unsaturation containing from 1 to 6 carbon atoms, M' is H or M, and Q is a divalent organic radical which is bonded to a silicon atom by way of a silicon-carbon bond; all remaining silicon valences of the silicon hydride and of the dioxolane-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms and divalent radicals joining silicon atoms.

In the above formula for the aliphatically unsaturated dioxolane compound (i) Q' denotes a monovalent, aliphatically unsaturated organic radical. While Q' can be any monovalent organic radical containing aliphatic unsaturation which is hydrosilylatable, i.e. reactive with a silicon hydride, hereinafter delineated, it is preferably an olefinically unsaturated radical. Q' is preferably terminally unsaturated, i.e. it has the structure $CH_2=CH-$ where the open valence is bonded directly or indirectly to the #4 atom, based on the International Union of Pure and Applied Chemist (IUPAC) Standard, of the dioxolane moiety.

Optionally, Q' can contain, in addition to carbon and hydrogen, other atoms commonly found in divalent radicals which serve only to link a silicon atom with a specifically selected moiety. Said other atoms include, for example, aprotic oxygen, sulfur and nitrogen atoms. Examples of aprotic O, N and S atoms include oxygen atoms of ethers, esters, amides and ketones; nitrogen atoms of amides and tertiary amines; and the sulfur atoms of thioethers, thioesters and thioketones.

Examples of preferred Q' radicals include $CH_2=CHCH_2OCH_2-$, $CH_2=CH-$, $CH_2=CHCH_2-$, $CH_2=CHCH_2CH_2-$, and $CH_2=CHOCH_2-$.

The M radicals of dioxolane (i) can be any monovalent hydrocarbon radical having from 1 to 6 carbon atoms. They typically have their origin in an aldehyde or ketone that was used to prepare the dioxolane moiety. Therefore they are radicals that allow the facile reaction of the aldehyde or ketone with, for example, a 1,2-diol to form the dioxolane moiety. They are also, for the purposes of this invention, radicals that will allow the facile removal of an aldehyde or ketone molecule from the dioxolane ring at an appropriate time in order to provide diol compounds of this invention.

Examples of M radicals include methyl, ethyl, isopropyl, phenyl and cyclohexyl. M' radicals are either hydrogen atoms or M radicals. M and M' can be the same or different, as desired; however, M and M' are preferably both hydrocarbon radicals and most preferably methyl radicals.

Examples of suitable aliphatically unsaturated dioxolanes (i) for the method of this invention include

$$CH_2=CHCH_2OCH_2CHOCPhH$$
$$|\quad\quad|$$
$$CH_2\ O$$

wherein Me denotes the methyl radical and Ph denotes the phenyl radical.

Dioxolanes used in this invention can be prepared from 1,2-diols and either an aldehyde such as acetaldehyde or benzaldehyde, thus forming dioxolanes which are cyclic acetals, or a ketone such as acetone or acetophenone, thus forming dioxolanes which are cyclic ketals.

The silicon hydride compound (ii) can have any structure provided that it contains an average of at least one silicon-bonded hydrogen atom per molecule that is available for participation in hydrosilylation. Examples of suitable silicon hydride compounds include silane hydrides and silicon hydrides containing a plurality of silicon atoms such as siloxane hydrides, silcarbane hydrides and siloxanesilcarbane hydrides.

Any silicon valences of the silicon hydride that are not satisified by hydrogen atoms are satisfied by radicals free of aliphatic unsaturation selected from the group consisting of monovalent hydrocarbon radicals, monovalent halohydrocarbon radicals, monovalent hydrolyzable radicals and divalent radicals joining silicon atoms.

Examples of said divalent radicals joining silicon atoms include oxygen atoms, which provide siloxane bonds; nitrogen atoms, which provide silazane bonds; and aliphatically saturated hydrocarbon, hydrocarbon ether, halohydrocarbon ether and halohydrocarbon radicals, which provide silcarbane bonds. The divalent radicals can be the same or different, as desired; however, they are preferably all oxygen atoms. That is, silicon hydrides (ii) containing a plurality of silicon atoms are preferably siloxane hydrides.

Examples of said monovalent hydrocarbon radicals, herein also referred to as R radicals, include alkyl radicals having from 1 to 20 carbon atoms, such as $CH_3-$, $CH_3CH_2-$, $(CH_3)_2CH-$, $C_6H_{13}-$, $C_8H_{17}-$, $C_{10}H_{21}-$ and $C_{20}H_{41}-$; cycloaliphatic radicals having from 3 to 8 carbon atoms, such as cyclohexyl; aryl radicals having from 6 to 20 carbon atoms, such as phenyl, tolyl, xylyl, anthracyl and xenyl; and aralkyl radicals having from 7 to 20 carbon atoms, such as benzyl and 2-phenylethyl. Typical monovalent hydrocarbon radicals for the purposes of this invention are methyl and phenyl.

Examples of said monovalent halohydrocarbon radicals, herein also referred to as R radicals, include any monovalent hydrocarbon radical delineated above wherein one or more of the hydrogen atoms therein have been replaced with a halogen atom, preferably fluorine or chlorine, but also including bromine and other halogen atoms. Preferred examples thereof include chloroalkyl radicals, such as chloropropyl and chloroisobutyl; fluoroalkyl radicals, such as $C_nF_{2n+1}CH_2CH_2-$ wherein n has a value of from 1 to 10; and halophenyl radicals, such as chlorinated and/or fluorinated phenyl radicals.

Examples of said monovalent hydrolyzable radicals, herein also referred to as Z radicals, include halogen atoms, preferably chlorine; alkoxy radicals, preferably methoxy, ethoxy and isopropoxy; alkoxyalkoxy radicals, such as methoxyethoxy, ethoxyethoxy and methoxyisopropoxy; amido radicals, such as acetamido and N-methylacetamido; and oximo, such as methylethylketoximo.

The silicon hydride (ii) can be any silane hydride having the formula $R_aSiHZ_{(3-a)}$; wherein Z and R denote the above-delineated monovalent hydrolyzable radical and monovalent hydrocarbon and halohydrocarbon radical, respectively, including preferred examples. The value of a can be 0, 1, 2 or 3, thereby encompassing silane hydrides ranging from $R_3SiH$ to $Z_3SiH$. When present, Z is preferably chlorine and R is methyl.

Examples of suitable silane hydrides for the purposes of this invention include $R_3SiH$, such as $Me_3SiH$, $Me_2PhSiH$, $Ph_2MeSiH$, $C_4F_9CH_2CH_2(Me)_2SiH$ and $CF_3CH_2CH_2(Me)_2SiH$; $R_2SiClH$, such as $Me_2SiClH$, $MePhSiClH$, $Ph_2SiClH$, $C_4F_9CH_2CH_2(Me)SiClH$ and $CF_3CH_2CH_2(Me)SiClH$; $RSiCl_2H$, such as $MeSiCl_2H$, $PhSiCl_2H$, $C_4F_9CH_2SiCl_2H$ and $CF_3CH_2CH_2SiCl_2H$; and $Cl_3SiH$.

The silicon hydride (ii) also can be any siloxane hydride containing at least one siloxane unit having the formula $R_bHSiO_{(3-b)/2}$ and any other siloxane units, if present, having the formula $R_cSiO_{(4-c)/2}$. R denotes the above-delineated monovalent hydrocarbon and halohydrocarbon radical, including preferred examples thereof.

The value of b can be 0, 1 or 2 and the value of c can be 0, 1, 2 or 3, thereby allowing for siloxane units ranging from trisubstituted, i.e. chain-terminating, units to unsubstituted, i.e. network, units.

Examples of typical siloxane units that can be present in the siloxane hydride (ii) include $R_3SiO_{\frac{1}{2}}$ units, such as $Me_3SiO_{\frac{1}{2}}$, $PhMe_2SiO_{\frac{1}{2}}$ and $CF_3CH_2CH_2Me_2SiO_{\frac{1}{2}}$; $R_2SiO_{\frac{1}{2}}$ units, such as $HMe_2SiO_{\frac{1}{2}}$ and $HPhMeSiO_{\frac{1}{2}}$; $R_2SiO_{2/2}$ units, such as $Me_2SiO_{2/2}$, $MePhSiO_{2/2}$, $CF_3CH_2CH_2MeSiO_{2/2}$, $Ph_2SiO_{2/2}$ and $CF_3CF_2CF_2CF_2CH_2CH_2MeSiO_{2/2}$; $RHSiO_{2/2}$, such as $MeHSiO_{2/2}$, $CF_3CH_2CH_2(H)SiO_{2/2}$, $PhHSiO_{2/2}$ and $C_4F_9CH_2CH_2(H)SiO_{2/2}$; $RSiO_{3/2}$ units, such as $MeSiO_{3/2}$, $PhSiO_{3/2}$, $CF_3CH_2CH_2SiO_{3/2}$ and $CF_3CF_2CF_2CF_2CH_2CH_2SiO_{3/2}$; $HSiO_{3/2}$; and $SiO_{4/2}$.

While the siloxane hydride (ii) can have any physical form such as a gas, liquid or solid form and any chemical structure such as a linear, cyclic, branch or network structure, it is preferably a liquid material having a linear or cyclic structure described by the formula

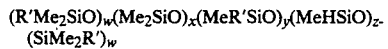
$(R'Me_2SiO)_w(Me_2SiO)_x(MeR'SiO)_y(MeHSiO)_z(SiMe_2R')_w$ wherein R' denotes a radical selected from the group consisting of said R radicals and hydrogen atoms.

Linear and cyclic siloxane hydrides are preferred as a siloxane hydride reactant (ii) for the preparation dioxolane-containing siloxanes because they provide liquid curable diacrylate-containing compounds compositions which are effective as a curable component in coating compositions, particularly adhesive-release coating compositions.

In this formula the values of x, y, z and x+y+z have average values of zero or more and both w have a value of zero or 1, with the proviso that there is an average of at least one silicon-bonded hydrogen atom per molecule of siloxane hydride.

For example, for linear siloxane hydrides having the above formula each w has a value of 1 and x+y+z has an average value of 0 or more, thereby providing a siloxane hydride having the formula $R'Me_2SiO(Me_2SiO)_x(MeR'SiO)_y(MeHSiO)_zSiMe_2R'$ and a viscosity of as little as 1 centistoke to as much as several million centistokes at 25° C.

Preferred examples of said linear siloxane hydrides include $Me_3SiO(Me_2SiO)_x(MeHSiO)_zSiMe_3$;

$HMe_2SiO(Me_2SiO)_xSiMe_2H$ and $HMe_2SiO(Me_2SiO)_x(MeHSiO)_zSiMe_2H$, wherein z has a value of from 1 to, for example, 50 and x has a value of from, for example, zero to several hundred.

Additional examples of said linear siloxane hydrides include

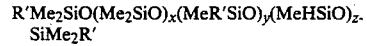
$Me_3SiO(Me_2SiO)_x(MeRSiO)_y(MeHSiO)_zSiMe_3$;

$HMe_2SiO(Me_2SiO)_x(MeRSiO)_ySiMe_2H$ and $HMe_2SiO(Me_2SiO)_x(MeRSiO)_y(MeHSiO)_zSiMe_2H$, wherein R denotes, for example, a phenyl radical, an alkyl radical or a fluorinated radical such as $CF_3CH_2CH_2$— or $CF_3CF_2CF_2CF_2CH_2CH_2$—, x has a value of from, for example, zero to several hundred, y has a value of from 1 to, for example, several hundred and z has a value of from 1 to, for example, 50.

For cyclic siloxane hydrides having the above formula each w has a value of 0 and x+y+z has an average value of 3 or more, thereby providing liquid or low-melting siloxane hydrides having the formula $(Me_2SiO)_x(MeR'SiO)_y(MeHSiO)_z$ and a viscosity of as little as 1 centistoke at 25° C.

Examples of said cyclic siloxane hydrides include $(Me_2SiO)_x(MeHSiO)_z$ and $(Me_2SiO)_x(MeRSiO)_y(MeHSiO)_z$;

wherein R denotes, for example, a phenyl radical, an alkyl radical or a fluorinated radical such as $CF_3CH_2CH_2$— or $CF_3CF_2CF_2CF_2CH_2CH_2$—, x has a value of from, for example, zero to 10, y has a value of from 1 to, for example, 10 and z has a value of from 1 to, for example, 10. Poly(methylhydrogen) cyclosiloxanes having up to 10 silicon atoms are preferred cyclic siloxane hydrides.

The silicon hydride (ii) also can be any silcarbane hydride or siloxane-silcarbane hydride. Silcarbane hydrides are known compounds similar in structure to siloxane hydrides wherein the oxygen atom bonding silicon atoms has been replaced with a divalent organic radical, thereby providing silicon-carbon bonding rather than silicon-oxygen bonding in the polymer backbone. Typical examples of said divalent organic radicals have been noted above. Typical examples of silcarbane hydrides include silethylene hydrides and silphenylene hydrides.

In addition to the above-delineated compounds, silicon hydride (ii) can also comprise silicon compounds containing silicon atoms bearing more than one hydrogen atom; however, such silicon multihydrides are more difficult to handle than the silicon hydrides delineated above.

The hydrosilylation catalyst (iii) can be any of the well known agents that are effective for facilitating the addition of the elements of the silicon-hydrogen linkage to a site of aliphatic unsaturation, particularly terminal olefinic unsaturation. Hydrosilylation catalysts include free radical initiators, photoinitiators and precious metal compounds.

Examples of suitable free radical initiators include, but are not limited to, redox pairs, perborates, percarbonates, photochemical systems, azo compounds such as azo-bis(isobutyronitrile), acyl peroxides such as benzoyl peroxide, alkyl peroxides such as di-t-butyl peroxide and hydroperoxides such as cumene hydroperoxide.

Examples of suitable photoinitiators include, but are not limited to, benzoin, benzoin alkyl ethers such as methyl, ethyl, isopropyl or isobutyl benzoin ether, acetophenone derivatives such as dialkoxyacetophenone such as diethoxyacetophenone, di- and trichloroacetophenones, α,α-dimethoxy-α-phenylacetophenone, 1-hydroxycyclohexylphenyl ketone, 2-hydroxy-2-methyl-1-phenylpropane-1-one, methylphenyl glyoxylate, 4-benzoylbenzyl-trimethylammonium chloride, α-acyloxime esters such as 1-phenyl-1,2-propanedione-2-(O-ethoxycarbonyloxime), thioxanthane and its derivatives, benzophenone in combination with a chain transfer agent such as a NH group and azo-bis(isobutyronitrile).

Examples of precious metal-containing compounds include, but are not limited to, platinum group metal-containing catalyst compounds. By platinum group it is meant herein ruthenium, rhodium, palladium, osmium, iridium and platinum. Component (iii) can be a platinum group metal; a carrier, such as silica gel or powdered charcoal, bearing a platinum group metal; or a compound or complex of a platinum group metal.

A preferred platinum-containing catalyst component in the method of this invention is a form of chloroplatinic acid, either as the commonly available hexahydrate form or as the anhydrous form, because of its easy dispersibility in organosilicon systems. A particularly useful form of chloro-platinic acid is that composition obtained when it is reacted with an aliphatically unsaturated organosilicon compound such as divinyltetramethyldisiloxane, as disclosed by Willing, U.S. Pat. No. 3,419,593 incorporated herein by reference.

The amount of hydrosilylation catalyst (iii) that is used in the method of this invention is not narrowly limited as long as there is a sufficient amount to accelerate a reaction between the silicon-bonded hydrogen atoms of silicon hydride (ii) with the aliphatic unsaturation of the dioxolane compound (i). The exact necessary amount of said catalyst component will depend upon the particular catalyst and is not easily predictable. However, for chloroplatinic acid said amount can be as low as one part by weight of platinum for every one million parts by weight of (i) plus (ii) preferably said amount is at least 10 parts by weight, on the same basis.

The relative amounts of dioxolane compound (i) and silicon hydride compound (ii) that are used in the method of this invention are not critical, the only requirement pertinent thereto being that there must be a sufficient amount of the former so that the product of the reaction contains an average of at least one silicon-bonded dioxolane radical having the above-stated formula.

The method of this invention can be practiced so that the product contains any number of unreacted silicon-bonded hydrogen atoms, in addition to said dioxolane radicals, if desired. Alternatively, the method can be practiced in such a manner that substantially all of the silicon-bonded hydrogen atoms have been reacted, if desired.

The required amounts of components (i) and (ii) can be calculated from a knowledge of the silicon-bonded hydrogen content of the silicon hydride, the desired number of silicon-bonded hydrogen atoms to be reacted and the stoichiometry of the following generalized hydrosilylation reaction:

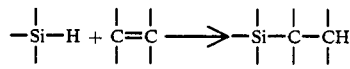

Although this reaction requires one site of aliphatic unsaturation for every silicon-bonded hydrogen atom to be reacted it is typical, especially when all silicon-bonded hydrogen atoms are to be reacted, that a slight excess of the former be used to insure that the reaction takes place to the desired extent.

The method of this invention can be practiced in any suitable manner that will cause said hydrosilylation to occur. For example, when the hydrosilylation catalyst (iii) comprises a platinum-containing material the reaction will generally occur at room temperature and nothing more than mere mixing of the required reactants is required. However, it is generally desired to accelerate the reaction further and heating can be advantageously used to this end.

One or more solvents can be mixed with reactants (i), (ii) and (iii), if desired, to facilitate the reaction and/or the handling of the reactants and/or the products. Said solvents must not interfere with the desired hydrosilylation reaction and preferably should not react with the reactants or products of this method.

Suitable solvents include the aliphatically saturated hydrocarbons, esters, ketones, halocarbons, ethers and alcohols that are commonly used in the organosilicon art. Examples thereof include hexane, toluene, xylene, ethyl acetate, methyl isobutyl ketone, trichloroethylene, diethyl ether, dioxane, ethylene glycol dimethyl ether, methanol, ethanol and isopropanol.

Said solvents can be used in the other aspects of this invention, delineated below with the same limitations relating to unreactivity.

In summary, the method of this invention, as above-delineated, comprises the formation of a dioxolane-substituted organosilicon compound containing at least one silicon-bonded dioxolane radical having the formula

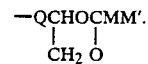

This invention further relates to the dioxolane-substituted organosilicon compounds, hereinafter delineated, that are prepared by this method.

Dioxolane-substituted organosilanes of this invention have the formula

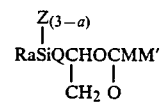

where Z is said monovalent hydrolyzable radical, a has a value of 0, 1, 2 or 3 and R is said monovalent hydrocarbon and halohydrocarbon radical. Preferred embodiments thereof include those organosilicon compound wherein Z is chlorine, R is Me and each of said dioxolane radicals has the formula

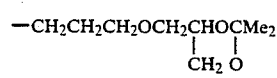

where Me is a methyl radical.

Dioxolane-substituted organosiloxanes of this invention contain at least one organosiloxane unit having the formula

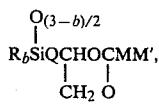

examples of which include the above-delineated siloxane hydride units where the silicon-bonded hydrogen has been replaced with a dioxolane radical. All other siloxane units therein, if any, have the formula $R_cH_dSiO_{(4-c-d)/2}$, such as those delineated above.

In the above unit formulae b has a value of 0, 1 or 2, c and c.d have values of 0, 1, 2 or 3, d has a value of 0 or 1 and R is said monovalent hydrocarbon and halohydrocarbon radical.

Preferred dioxolane-substituted organosiloxanes of this invention have the formula $(XMe_2SiO)_w(Me_2SiO)_x(MeXSiO)_y(MeHSiO)_z(SiMe_2X)_w$ where X is selected from the group consisting of R radicals, hydrogen atoms, and dioxolane radicals.

The average values of x, y and z can be zero or more, with the following provisos. For linear organosiloxaues each w has a value of 1 and x+y+z has an average value of zero or more and for cyclic organosiloxanes each w has a value of 0 and x+y+z has an average value of at least 3, there being an average of at least one of said silicon-bonded dioxolane radicals per molecule of organosiloxane. Each of said dioxolane radials preferably has the formula

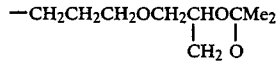

where Me is a methyl radical.

Examples of said preferred dioxolane-substituted organosilanes and organosiloxanes include those silane and siloxane hydrides delineated above wherein at least one of the silicon-bonded hydrogen atoms in each molecule has been replaced with a dioxolane radical, preferably

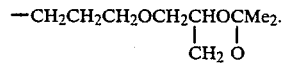

The following examples are disclosed to further illustrate, but not limit, the invention delineated by the appended claims. All parts and percentages are by weight and all temperatures are Celsius degrees unless otherwise stated. Me, Ph and Vi denote the methyl, phenyl and vinyl radicals, respectively.

All dioxolane-substituted organosilicon compounds were characterized by proton nuclear magnetic resonance spectroscopy (nmr) and by infrared spectroscopy (ir). They all showed two singlets at $\delta = 1.3$ (from tetramethylsilane) in the nmr and doublets at 1375 cm$^{-1}$ in the ir characteristic of the isopropylidene group of the methylenedioxolane moiety.

The following examples illustrate the preparation of dioxolane-substituted silanes of this invention using the method of this invention.

EXAMPLE I

Five parts of 4-allyloxymethyl-2,2-dimethyl-1,3-dioxolane and 0.002 parts of (PhC≡CC(OH)(CH$_3$)Ph)$_2$Pt, a hydrosilylation catalyst, were mixed in a flask fitted with a condenser, an addition funnel and a thermometer. Methyldichlorosilane, 3.5 parts, was added to the mixture via the addition funnel and the mixture was heated to 71°. At 78° a mild exotherm occurred which raised the reaction temperature to 91°. After the exotherm had subsided the reaction mixture was distilled at reduced pressure to give 6.5 parts of 4-(3'-methyldichlorosilylpropoxymethyl)-2,2-dimethyl-1,3-dioxolane having a boiling point of 100° to 103° at 0.7 Torr.

The 4-allyloxymethyl-2,2-dimethyl-1,3-dioxolane was prepared by mixing acetone, 225 parts, 3-allyloxy-1,2propanediol, 195 parts and toluene, 480 parts in a flask fitted with a magnetic stirring bar and a water trap mounted with a reflux condenser. Concentrated sulfuric acid, 4 parts, was added to the flask and the mixture was heated to reflux. The first 170 parts of distillate were removed via the water trap, after which reflux was conducted and water was collected in the water trap. After 13 hours the reaction mixture was cooled, neutralized with solid sodium bicarbonate, distilled to remove water and toluene and then distilled under vacuum to give 161 parts of 4-allyloxymethyl-2,2-dimethyl-1,3-dioxolane having a boiling point of 57° to 58° at 4.5 Torr.

EXAMPLE II

Five parts of 4-allyloxymethyl-2,2-dimethyl-b 1,3-dioxolane and 0.002 parts of (PhC≡CC(OH)(CH$_3$)Ph)$_2$Pt were mixed in a flask fitted with a condenser, an addition funnel and a thermometer. Dimethylchlorosilane, 5 parts, was added to the mixture via the addition funnel and the mixture was heated to 70° for 25 minutes. The reaction mixture was then cooled and distilled at reduced pressure to give 5.2 parts of 4-(3'-dimethylchlorosilylpropoxymethyl)-2,2-dimethyl-1,3-dioxolane having a boiling point of 98° to 105° at 0.7 Torr.

The following examples illustrate the preparation of dioxolane-substituted organosiloxanes of this invention using the method of this invention.

EXAMPLE III

Twenty parts of 4-allyloxymethyl-2,2-dimethyl-1,3-dioxolane, 0.006 parts of a hydrosilylation catalyst containing 4% platinum and being prepared according to the method of Willing, U.S. Pat. No. 3,419,593, and 80 parts of a hydrogen-terminated polydimethylsiloxane containing an average of about 20 silicon atoms per molecule were mixed in a flask. A mild exotherm took place which raised the temperature of the reaction mixture to 70° and external heating was used to keep it there for 5 hours. An infrared spectrum of the reaction mixture taken after five hours showed that no silicon-bonded hydrogen atoms remained. The product was assigned the structure XMe$_2$SiO(Me$_2$SiO)$_{18}$SiMe$_2$X wherein X denotes

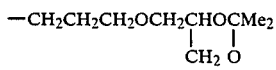

based on the spectroscopic data and the nature of the hydrosilylation reaction.

EXAMPLE IV

Twenty five and 9/10 parts of 4-allyloxymethyl-2,2-dimethyl-1,3-dioxolane, 0.02 parts of the hydrosilylation catalyst described in Example III and 41.4 parts of a hydrogendimethylsiloxane-terminated polydimethylsiloxane-co-methylhydrogensiloxane containing an average of about 14 dimethylsiloxane units and 2 methylhydrogensiloxane units per molecule were mixed in a flask. A mild exotherm took place and external heating was used to keep the temperature of the reaction mixture at 70° for 24 hours. An infrared spectrum of the reaction mixture taken after 24 hours showed that no silicon-bonded hydrogen atoms remained. The product was assigned the structure $$XMe_2SiO(Me_2SiO)_{14}(MeXSiO)_2SiMe_2X$$

wherein X denotes

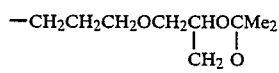

based on the spectroscopic data and the nature of the hydrosilylation reaction.

Such dioxolane-containing silicon compounds are disclosed in copending applications U.S. Ser. Nos. 06/914,899, filed June 3, 1986, and 07/338,831, filed Apr. 14, 1989, both assigned to the same assignee as this application. The dioxolane-containing silicon compounds of the two prior applications are converted to diol-containing and then to diacrylate-containing silicon compounds which are used in curable compositions for providing a substrate with an adhesive release coating.

The following examples illustrate additional procedures for the preparation of dioxolane or ketal functional silicones which may be employed in order to impart durable hydrophilicity to cotton fabric. These ketal functional silicones were prepared by the platinum catalyzed reaction of a silicon hydride with 4-allyloxymethyl-2,2-dimethyl-1,3-dioxolane of the formula

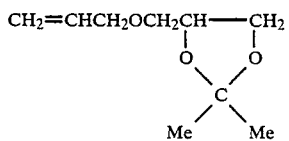

where Me is methyl,

For example, Examples VII and VIII illustrate the preparation respectively of the following compounds:

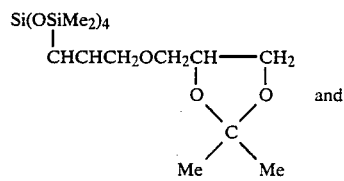

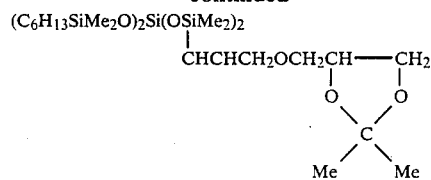

where Me is methyl.

EXAMPLE V

Preparation of Sym(2,2-dimethyl-4-methyloylpropyl-1,3-dioxolane)-tetramethyldisiloxane, dp=2

A 500 ml 3-necked round bottom flask was fitted with a magnetic stirrer, thermometer, addition funnel and water condenser. To this was charged 75 grams (0.43 mol) of 3-allyloxy-1,2-(dimethyl ketal)propane (hereafter called KETAL) containing 5 mg (7.0×10$^{-3}$ mmol) (PhC≡CMe(OH)Ph)$_2$Pt (hereafter called PTCAT). This mixture was heated to 95° C. after which a portion of 25 grams (0.19 mol) HMe$_2$SiOSiMe$_2$H was added, resulting in a temperature rise to 144° C. within 5 minutes. The remainder of the HMe$_2$SiOSiMe$_2$H was added over the next 8 minutes between 144° to 155° C. by controlling the rate of addition. The reaction mixture was allowed to cool to about 75° C. and was held between 75° to 80° C. by external heating for 3 hours. dP is defined as degree of polymerization.

Approximately 1 gram each of Nu-Char activated carbon and fillers earth were added to the crude mixture, stirred one hour, allowed to sit overnight and filtered through celite under vacuum to a water white fluid. The fluid was stripped of volatiles under vacuum. A total of 75.7 grams of residue remained as a slight brownish tint fluid. The fluid was treated with Nu-Char and fullers earth and filtered through celite to a water white fluid with a viscosity of 18.52 Centistoke at 25° C.

EXAMPLE VI

Preparation of Sym(2,2-dimethyl-4-methyloylpropyl-1,3dioxolane) Polydimethylsiloxane, dp=15

The apparatus described in Example V was charged with 100 grams (0.091 mol) of HMe$_2$SiO(Me$_2$SiO)$_{1-3}$SiMe$_2$H to which was added 33.35 grams (0.19 mol) of KETAL containing 6 mg (9.0×10$^{-3}$ mmol) of PTCAT at room temperature over a 9 minute period. An exotherm to 68° C. occurred within the first 3 minutes. The temperature was not allowed to exceed 74° C. by controlling the rate of silicone hydride addition. The reaction mixture was heated at 65° to 70° C. for 1.5 hours and allowed to cool to room temperature. After sitting overnight, the fluid was treated with approximately 1 gram each of Nu-Char and fillers earth and filtered under vacuum, followed by stripping of the volatiles to 135° C. and 1 mm Hg to a water white fluid with a viscosity of 35.8 centistoke at 25° C.

EXAMPLE VII

Preparation of
Tetrakis[(2,2-dimethyl-4-methyloylpropyl-1,3-dioxolane)dimethylsiloxy]silane a Tetra-functional Ketal Siloxane Fluid A 250 ml 3-necked round-bottom flask was fitted with a magnetic stirrer, thermometer, addition funnel and water condenser and charged with 57.52 grams (0.334 mol) of KETAL and 10 mg ($1.5 \times 10^{-2}$ mmol) of PTCAT. To this solution was added 25 grams (0.076 mol) of $Si(OSiMe_2H)_4$ over a 28 minute period. Within the first 2 minutes an exotherm to 126° C. occurred which did not maintain itself as the addition progressed. After the addition was completed, external heat was applied to maintain a 82° C. temperature for 1 hour. The fluid was stripped of volatiles under vacuum to 107° C. at 1.3 mm Hg. The residue, 75.1 grams of hazy grayish fluid, was treated with Nu-Char and fillers earth and filtered through celite under vacuum to a water white fluid with a viscosity of 60.1 centistoke at 25° C.

EXAMPLE VIII

Preparation of
Bis(hexyldimethylsiloxy)-Bis[(2,2-dimethy]-4-methyloylpropyl-1,3-dioxolane)dimethylsiloxy]silane a Bis(hexyl)-Di-functional Ketal Siloxane Fluid The apparatus described in Example VII was charged with 150 grams of toluene and 50 grams (0.152 mol) of $Si(OSiMe_2H)_4$ to which was added a mixture of 25.58 grams (0.30 mol) of 1-hexene and 52.66 grams (0.304 mol) of KETAL containing 9.6 mg ($1.5 \times 10^{-2}$ mmol) of PTCAT over a 1.25 hour period at a temperature of 65° C. An exotherm to 80° C. was observed which did not sustain itself as the addition of the silicone hydride progressed. When the temperature had fallen to 72° C., the reaction mixture was heated to 100° C. for the last 0.5 hour of the addition. Heat was maintained for approximately 10 hours as 100° to 102° C. The flask was stripped of volatiles to 145° C. and 0.5 mm Hg vacuum. A yellow hazy fluid remained which was treated with 1 gram each of Nu-Char and fillers earth and filtered under vacuum to 107.8 grams of a water white fluid with a viscosity of 22.44 centistoke at 25° C.

Ketal functional silicone materials were evaluated as durable hydrophilic textile treatments by evaluating the water absorbance time and the durability of the compounds. The fabric selected for the evaluation was a woven sixty-five percent polyester and thirty-five percent cotton fabric. Samples of the fabric were dipped in a treatment bath containing one percent by weight of the ketal functional silicone dissolved in xylene. The bath size was about fifty grams, and the fabric wet pick-up was about ninety percent for all of the fabric samples treated. After padding, the fabric samples were dried at 177 degrees Centigrade for ninety seconds and allowed to relax on a clothes line for twenty-fours hours prior to being evaluated for water drop absorbance time and durability. The water drop absorbance time was evaluated by placing a drop of water on the horizontal fabric surface and measuring the time required for the water drop to be absorbed into the fabric. Samples which exhibited water drop absorbance times of less than one minute were considered hydrophilic, and were further evaluated for durability. Control samples not considered hydrophilic yielded water drop absorbance times well in excess of three minutes. The durability of the samples providing water drop absorbance times of less than one minute was further evaluated by washing and drying the samples, and re-measuring the water drop absorbance time. A treatment was considered durable if the water drop absorbance time following the washing and drying remained less than one minute, and was not significantly different from the pre-washed water drop absorbance time. Table I indicates that the ketal functional organosilicon compounds of the present invention provide good water absorbance time initially and following one and five washes, and therefore are useful as durable hydrophilic textile treatments

TABLE I

| Material | Water Drop Absorbance Time (sec.) |
| --- | --- |
| 2 DP, 100 mole percent ketal functional siloxane | 21.0 |
| One wash | 12.5 |
| Five washes | 6.5 |
| 100 DP, 2 mole percent ketal functional siloxane | 19.0 |
| One wash | 41.0 |
| Five washes | 23.0 |

It will be apparent from the foregoing that many other variations and modifications may be made in the structures, compounds, compositions, articles of manufacture, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A method of treating textiles in order to increase the water absorptivity of the textiles comprising contacting the textiles with an effective amount of a dioxolane-substituted organosilicon compound containing at least one silicon-bonded dioxolane radical having the formula

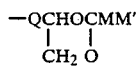

where Q is a divalent organic radical which is bonded to the silicon atom by way of a silicon-carbon bond, M is a monovalent hydrocarbon radical free of aliphatic unsaturation containing from 1 to 6 carbon atoms and M' is H or M; all remaining silicon valences of the dioxolane-substituted organosilicon compound being satisfied by radicals free of aliphatic unsaturation selected from the group consisting of monovalent hydrocarbon radicals, monovalent halohydrocarbon radicals, monovalent hydrolyzable radicals, hydrogen atoms and divalent radicals joining silicon atoms.

2. The method of claim 1 wherein the organosilicon compound has the formula

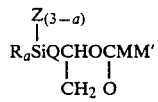

where Z is said monovalent hydrolyzable radical, a has a value of 0, 1, 2 or 3 and R is said monovalent hydrocarbon and halohydrocarbon radical.

3. The method of claim 2 wherein Z is chlorine, R is Me and each of said dioxolane radicals has the formula

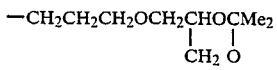

where Me is a methyl radical.

4. The method of claim 1 wherein the organosilicon compound has the formula

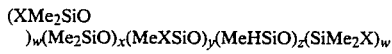

where Me is methyl, X is selected from the group consisting of R radicals, hydrogen atoms, and dioxolane radicals, x, y and z have average values of 0 or more and, for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded dioxolane radicals per molecule of organosiloxane.

5. The method of claim 4 wherein each of said dioxolane radicals has the formula

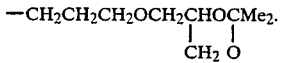

6. A method of treating textiles in order to increase the water absorptivity of the textiles comprising contacting the textiles with an effective amount of a ketal functional organosilicon compound of the formula selected from the group consisting of

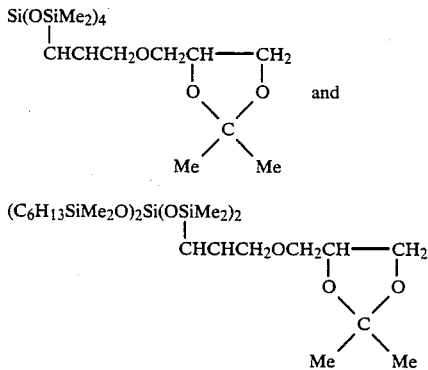

where Me is methyl.

7. A method of treating textiles in order to increase the water absorptivity of the textiles comprising contacting the textiles with an effective amount of a ketal functional organosilicon compound selected from the group consisting of sym(2,2-dimethyl-4-methyloylpropyl-1,3-dioxolane)tetramethyldisiloxane and sym(2,2-dimethyl-4-methyloylpropyl-1,3-dioxolane) polydimethylsiloxane.

8. A method of treating textiles in order to increase the water absorptivity of the textiles comprising contacting the textiles with an effective amount of a dioxolane-substituted organosiloxane compound containing at least one silicon-bonded dioxolane radical having the formula

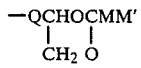

where Q is a divalent organic radical which is bonded to the silicon atom by way of a silicon-carbon bond, M is a monovalent hydrocarbon radical free of aliphatic unsaturation containing from 1 to 6 carbon atoms and M' is H or M; all remaining silicon valences of the dioxolane-substituted organosiloxane compound being satisfied by radicals free of aliphatic unsaturation selected from the group consisting of monovalent hydrocarbon radicals, monovalent halohydrocarbon radicals, monovalent hydrolyzable radicals, hydrogen atoms and divalent radicals joining silicon atoms.

9. The method of claim 8 wherein the organosiloxane compound has the formula

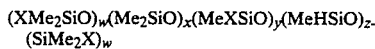

where Me is methyl, X is selected from the group consisting of R radicals, hydrogen atoms, and dioxolane radicals, x, y and z have average values of 0 or more and, for linear organosiloxanes each w has a value of 1 and x+y+z has an average value of 0 or more and for cyclic organosiloxanes each w has a value of 0 and x+y+z has an average value of at least 3, there being an average of at least one of said silicon-bonded dioxolane radicals per molecule of organosiloxane.

10. A method of treating textiles in order to increase the water absorptivity of the textiles comprising forming a treatment bath containing a dioxolane functional organosiloxane compound, of claim 8 contacting the textiles with the dioxolane functional organosiloxane compound in the treatment bath, removing the dioxolane functional organosiloxane treated textiles from the treatment bath, and drying the treated textiles.

11. The method of claim 10 wherein the treated textiles are padded prior to being dried.

12. The method of claim 10 wherein the treatment bath contains the dioxolane functional organosiloxane compound dissolved in a solvent.

13. The metho of claim 12 wherein the solvent is xylene and the treatment bath contains about one percent by weight of the dioxolane functional organosiloxane compound.

14. A method of treating textiles in order to increase the water absorptivity of the textiles comprising forming a treatment bath containing a dioxolane functional organosilicon compound, contacting the textiles with the dioxolane functional organosilicon compound in the treatment bath, removing the dioxolane functional organosilicon treated textiles from the treatment bath, and drying the treated textiles.

15. The method of claim 14 wherein the treated textiles are padded prior to being dried.

16. The method of claim 14 wherein the treatment bath contains the dioxolane functional organosilicon compound of claim 8 dissolved in a solvent.

17. The method of claim 16 wherein the solvent is xylene and the treatment bath contains about one percent by weight of the dioxolane functional organosilicon compound.

* * * * *